United States Patent
Uys et al.

(10) Patent No.: US 11,690,509 B2
(45) Date of Patent: Jul. 4, 2023

(54) SYSTEM AND METHOD FOR OBTAINING A PUPIL RESPONSE PROFILE

(71) Applicant: MEDICAL DIAGNOSTECH PTY LTD., Brackenfrell (ZA)

(72) Inventors: Ashley Thurston Uys, Capetown (ZA); Stefan Enthoven, Capetown (ZA); Kieran Eamon Duggan, Capetown (ZA); Kea Francis Barnes, Capetown (ZA)

(73) Assignee: MEDICAL DIAGNOSTECH PTY LTD., Brackenfell (ZA)

( * ) Notice: Subject to any disclaimer, the term of this patent is extended or adjusted under 35 U.S.C. 154(b) by 360 days.

(21) Appl. No.: 16/772,227

(22) PCT Filed: Dec. 13, 2017

(86) PCT No.: PCT/IB2017/057886
§ 371 (c)(1),
(2) Date: Jun. 12, 2020

(87) PCT Pub. No.: WO2019/116078
PCT Pub. Date: Jun. 20, 2019

(65) Prior Publication Data
US 2020/0337556 A1 Oct. 29, 2020

(51) Int. Cl.
*A61B 3/00* (2006.01)
*A61B 3/11* (2006.01)
(Continued)

(52) U.S. Cl.
CPC ............ *A61B 3/112* (2013.01); *A61B 3/0008* (2013.01); *A61B 3/0025* (2013.01); *A61B 3/145* (2013.01);
(Continued)

(58) Field of Classification Search
CPC ..... A61B 3/0008; A61B 3/0025; A61B 3/112; A61B 3/145; G06T 5/50; G06T 7/0012;
(Continued)

(56) References Cited

U.S. PATENT DOCUMENTS 5,784,145 A 7/1998 Ghodse et al.
6,022,109 A 2/2000 Dal Santo
(Continued)

FOREIGN PATENT DOCUMENTS

CN 101984453 A * 3/2011
CN 101872237 B * 4/2012
(Continued)

OTHER PUBLICATIONS

Viola et al. ("Robust Real-Time Face Detection," International Journal of Computer Vision 57(2), 137-154, 2004) (Year: 2004).*
(Continued)

*Primary Examiner* — Yubin Hung
(74) *Attorney, Agent, or Firm* — Cantor Colburn LLP

(57) ABSTRACT

A system and method are provided for obtaining a pupil response profile for a subject. The method include: obtaining scan data as frames of a pupil response over time prior to, during and after exposure to a flash of a light source; locating a candidate pupil to be measured from the scan data; image processing the scan data to obtain a set of pupil candidate measurements to generate a graph of pupil measurements against time; filtering the graph to produce a final set of pupil measurements forming a pupil response profile. The method may also include: measuring profile parameters from the pupil response profile; and using the profile parameters to determine aspects of the pupil response.

16 Claims, 11 Drawing Sheets

(51) Int. Cl.
*A61B 3/14* (2006.01)
*G06T 5/50* (2006.01)
*G06T 7/00* (2017.01)

(52) U.S. Cl.
CPC .............. *G06T 5/50* (2013.01); *G06T 7/0012* (2013.01); *G06T 2207/20024* (2013.01); *G06T 2207/20216* (2013.01); *G06T 2207/30041* (2013.01)

(58) Field of Classification Search
CPC . G06T 2207/20024; G06T 2207/20216; G06T 2207/30041
See application file for complete search history.

(56) References Cited

U.S. PATENT DOCUMENTS

| | | | |
|---|---|---|---|
| 6,116,736 A | 9/2000 | Stark et al. | |
| 6,820,979 B1 | 11/2004 | Stark et al. | |
| 7,147,327 B2 | 12/2006 | Stark et al. | |
| 7,625,087 B2 | 12/2009 | Taylor | |
| 9,357,966 B1 | 6/2016 | Cohen | |
| 10,417,495 B1* | 9/2019 | Davami | G06V 40/193 |
| 2003/0068097 A1* | 4/2003 | Wilson | G06F 17/18 |
| | | | 382/276 |
| 2003/0208125 A1* | 11/2003 | Watkins | A61B 3/12 |
| | | | 600/476 |
| 2004/0169817 A1* | 9/2004 | Grotehusmann | A61B 5/1171 |
| | | | 351/204 |
| 2005/0147291 A1* | 7/2005 | Huang | G06V 40/172 |
| | | | 382/218 |
| 2007/0041644 A1* | 2/2007 | Kim | G06V 40/165 |
| | | | 382/190 |
| 2008/0198330 A1 | 8/2008 | Taylor | |
| 2009/0174865 A1 | 7/2009 | Privitera et al. | |
| 2010/0060753 A1* | 3/2010 | Yamauchi | H04N 5/378 |
| | | | 348/241 |
| 2011/0077548 A1* | 3/2011 | Torch | A61B 5/165 |
| | | | 600/558 |
| 2011/0170064 A1 | 7/2011 | Taylor | |
| 2012/0242956 A1* | 9/2012 | Chernyak | A61B 3/112 |
| | | | 351/210 |
| 2014/0313488 A1* | 10/2014 | Kiderman | A61B 3/145 |
| | | | 351/246 |
| 2014/0320820 A1* | 10/2014 | Kumarasamy | A61B 3/112 |
| | | | 351/221 |
| 2015/0045012 A1* | 2/2015 | Siminou | H04W 4/80 |
| | | | 455/419 |
| 2016/0223819 A1* | 8/2016 | Liu | G06F 3/013 |
| 2016/0235295 A1* | 8/2016 | Sadhasivam | A61B 5/7275 |
| 2017/0318019 A1* | 11/2017 | Gordon | H04L 9/3226 |
| 2018/0144179 A1* | 5/2018 | Hatakeyama | G06V 40/171 |
| 2019/0302963 A1* | 10/2019 | Harrison | G06V 40/28 |
| 2020/0121237 A1* | 4/2020 | Yellin | A61B 5/163 |

FOREIGN PATENT DOCUMENTS

| | | | |
|---|---|---|---|
| CN | 104068824 A | * 10/2014 | |
| CN | 106022299 A | * 10/2016 | ............... G06K 9/00 |
| WO | 2004016153 A2 | 2/2004 | |
| WO | WO-2009046189 A1 | * 4/2009 | ............... A61B 3/12 |
| WO | WO-2014146199 A1 | * 9/2014 | ......... G02B 27/0093 |

OTHER PUBLICATIONS

Ebisawa et al. ("Head-Free, Remote Eye-Gaze Detection System Based on Pupil-Corneal Reflection Method With Easy Calibration Using Two Stereo-Calibrated Video Cameras," IEEE Transactions on Biomedical Engineering (vol. 60, Issue: 10, Oct. 2013); Date of Publication: Jun. 6, 2013) (Year: 2013).*
International search report issued in respect of PCT/IB2017/05886 dated Nov. 23, 2018, 3 pages.
Written opinion issued in respect of PCT/IB2017/05886, 6 pages.

* cited by examiner

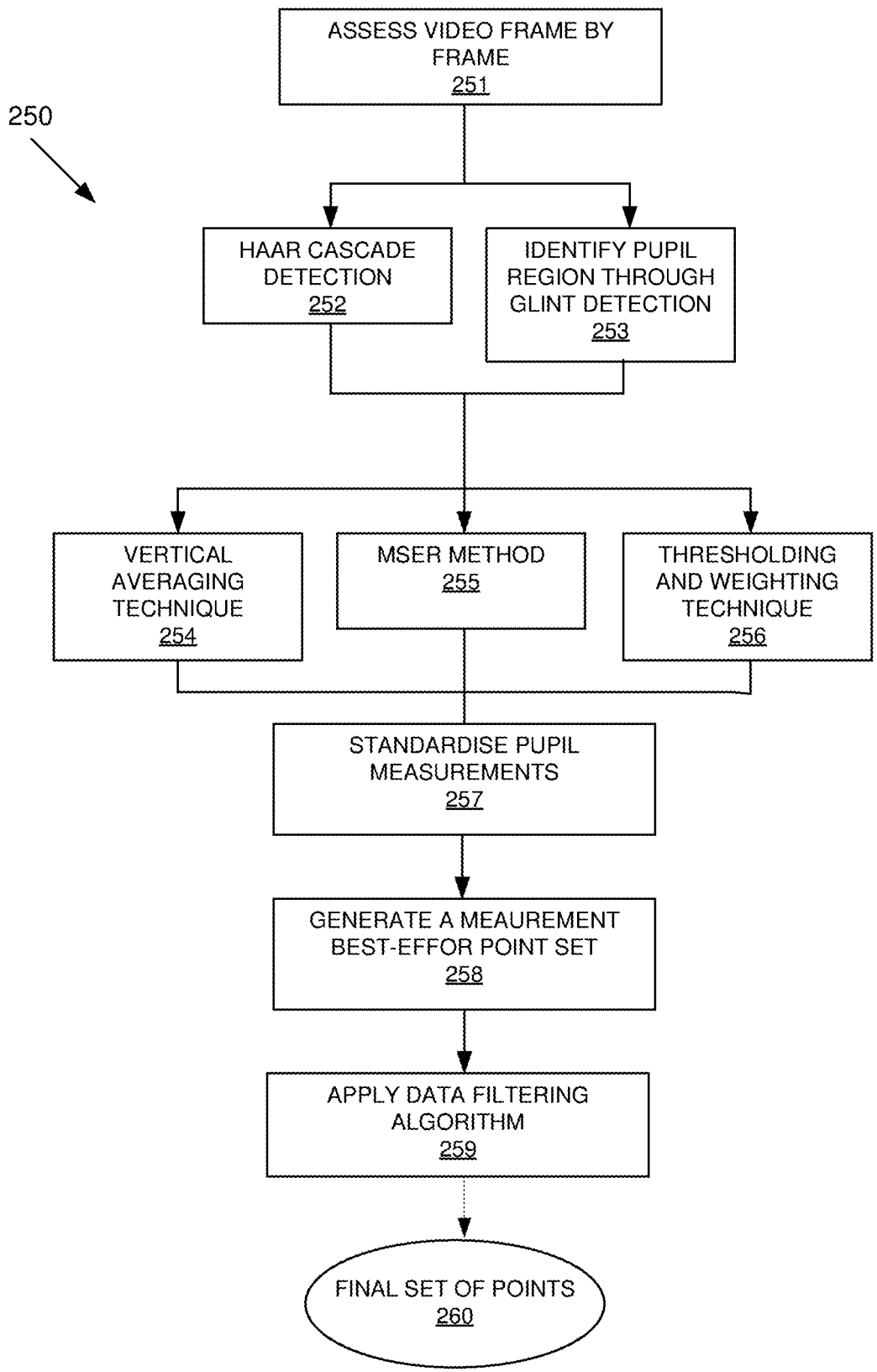

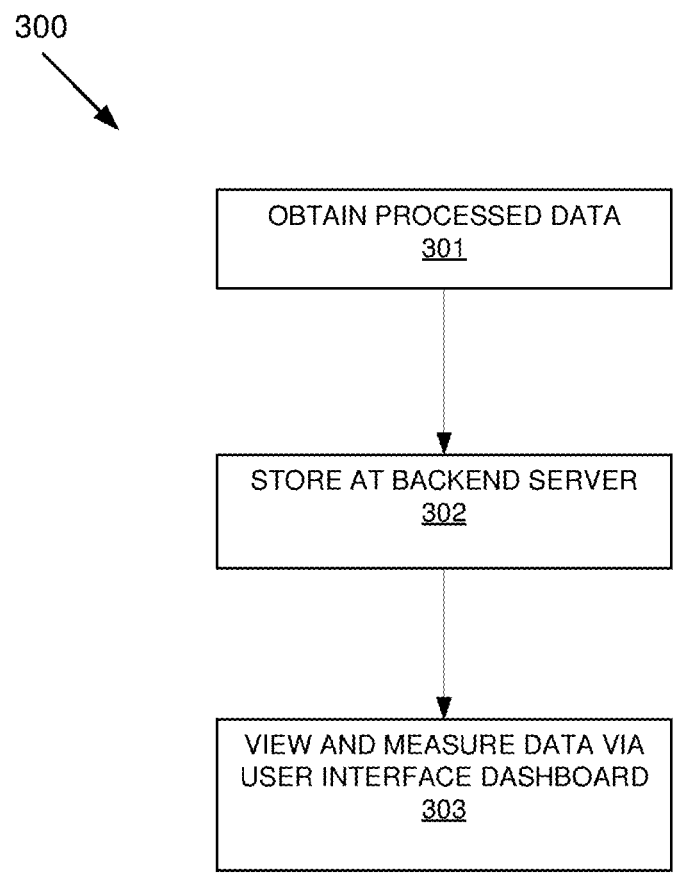

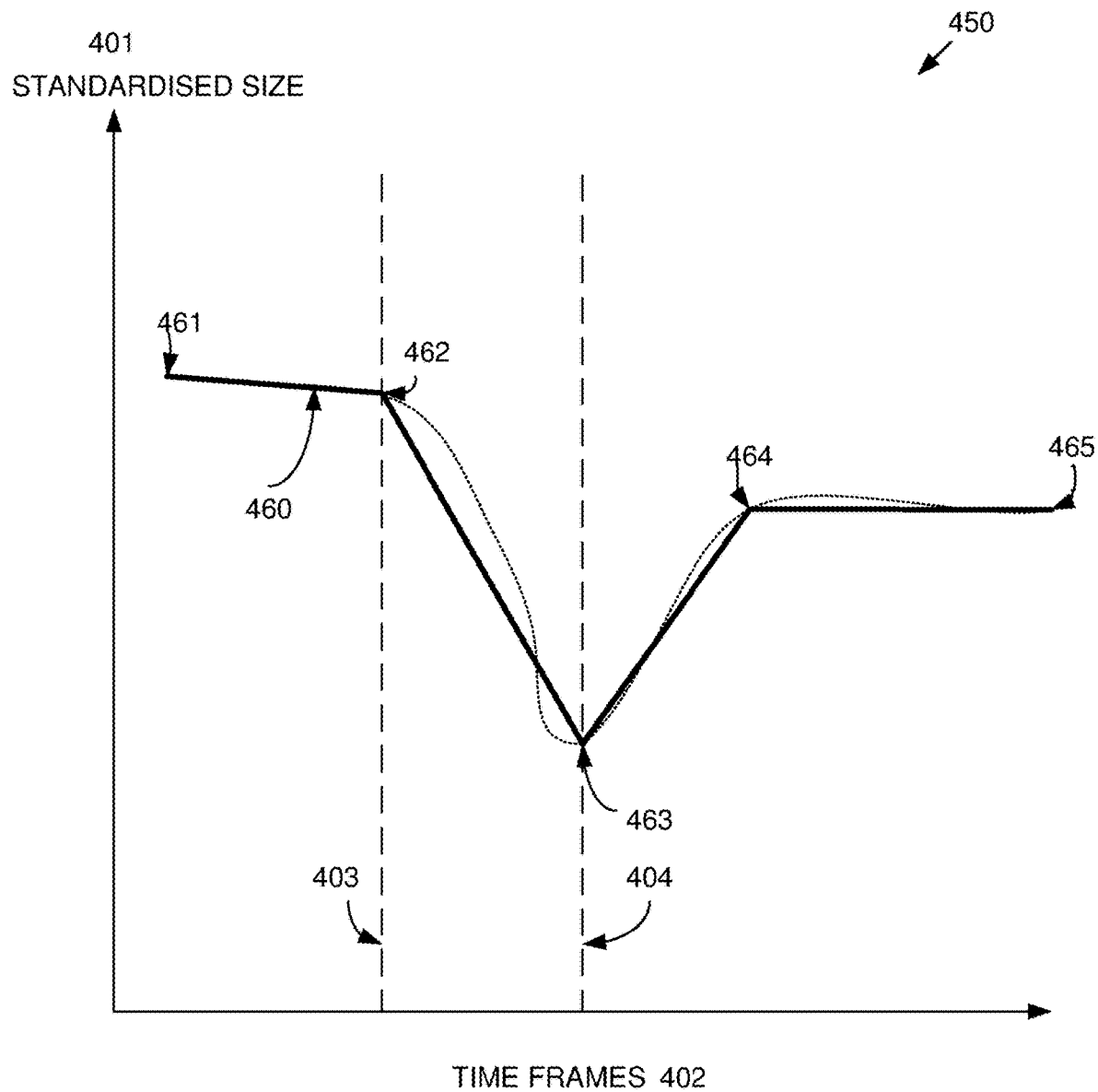

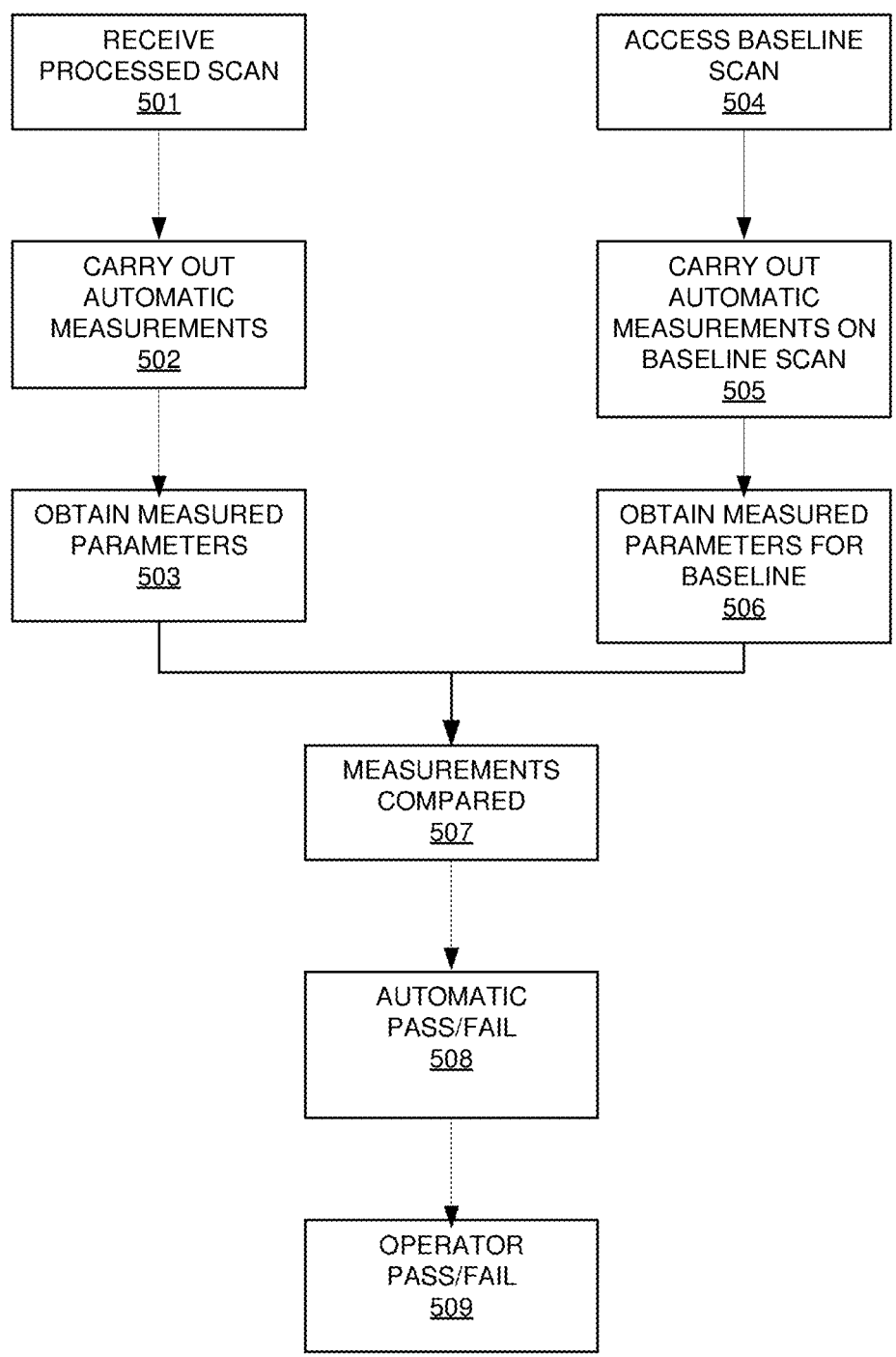

SYSTEM AND METHOD FOR OBTAINING A PUPIL RESPONSE PROFILE

CROSS REFERENCE TO RELATED APPLICATIONS

This application is a National Stage application of PCT/IB2017/057886, filed Dec. 13, 2017, which is incorporated are incorporated by reference in their entirety herein.

FIELD OF THE INVENTION

This invention relates to a system and method for obtaining a pupil response profile for a subject.

BACKGROUND TO THE INVENTION

Pupilometers are devices used to assess pupillary reflexes or responses to visual stimuli, typically light exposure. A variety of such pupilometers are currently available. Pupilometers are known that measure a left or a right eye's pupillary response individually, or which measures both sides at the same time.

When a patient's pupil is exposed to a light stimulus, the pupil response is not instantaneous due to a delay in the reaction of the iris sphincter muscle. Abnormal pupillary responses may point to a number of medical conditions which a subject may suffer from. For example, pupils which do not respond, or minimally respond, to light stimuli may indicate that the subject is under the influence of a drug or medicament, for example ecstasy or alcohol. Similarly, a sleep disorder or fatigue, Alzheimer's, Parkinson's, disease of the retina or optic tract, Homer's syndrome, systemic autonomic neuropathy associated with certain types of diabetes, melancholy, schizophrenia, stress, etc. may be indicated by abnormal pupillary response. A difference or specific relationship between the reaction of a left side pupil and right side retina may also point to specific conditions, for example relative afferent pupillary defect.

As abnormal pupillary response rates may indicate a variety of conditions of a person, measuring accuracy is of utmost importance to avoid incorrect detection or suspicion of a condition, which may lead to either unnecessary medical tests, or which may lead to a misdiagnosis, no diagnosis of a condition, or to a condition remaining undiagnosed. This can lead to prescribing of incorrect medication as the condition is misdiagnosed as well as the progression of a condition if it remains undiagnosed.

In some pupilometers, image analysis is performed on a still image or a video frame taken of a subject's eye or eyes in order to detect a subject's pupils. This may be done by extracting the dimensions of generally round shapes present in the image or frame. The generally round shapes present in a subject's eyes can be expected to include the iris and the pupil. Due to a number of reasons, including reflection of the light source and false round shapes which may be present in an image taken of a subject's eye, or the area surrounding a subject's eye, round shapes may be measured which are not in fact the desired measurements.

If only the dimensions of the iris and pupil could be measured per eye, it would be relatively simple to identify the larger dimension (which would be the iris), and the smaller dimension (which would be the pupil) for the purpose of calculating pupillary response. However, as image analysis typically pick up additional round shapes, the method is not as simple.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

According to an aspect of the present invention there is provided a computer-implemented method for obtaining a pupil response profile of a subject, comprising: obtaining scan data as frames of a pupil response over time prior to, during and after exposure to a flash of a light source; locating a candidate pupil to be measured from the scan data; image processing the scan data to obtain a set of pupil measurements to generate a graph of pupil measurements against time; filtering the graph to produce a final set of pupil measurements forming a pupil response profile; measuring profile parameters from the pupil response profile; and using the profile parameters to determine aspects of the pupil response.

The method may include: applying a pupil locating light source of a given shape for a defined period to a subject; and subsequently applying a flash of a visible light source to the subject; wherein obtaining scan data obtains one or more frames with a reflection of the pupil locating light source in an imaged pupil and multiple frames of the imaged pupil prior to, during and after exposure to the flash of a visible light source.

Locating a candidate pupil may include obtaining scan data of a reflection of a pupil locating light source of a given shape from the surface of an eye and locating a pupil identifies a generally circular image including a reflection of the given shape. In one embodiment, the pupil locating light source is an infra-red light source.

A HAAR cascade eye detection may be used if a reflection is not detected in the scan data. The method may include: standardising the pupil measurements by using a ratio of a measured pupil size and an estimated pre-calculated ratio of the distance from a camera capturing device to a surface of a subject's eye. Alternatively, the method may include: standardising the pupil measurements by using a ratio of a measured pupil size and a measured distance between reflections in the scan data of two eyes of a subject.

The graph may be a point graph and filtering the graph may use a running averaging filter to average to at most a single pupil measurement per eye per time frame, making use of a standard deviation limit on average deviation to eliminate graph fluctuations and erroneous data caused by the partial or complete covering of the pupil by the subject's eyelid. Filtering the graph may remove noisy measurements through the implementation of a spline line of best fit on the pre-filtered data.

Image processing may include one or more or a combination of: maximally stable external region (MSER), grayscale thresholding, and image column summing and averaging methods to measure pupils.

Measuring profile parameters from the pupil response profile may include measuring one or more of the group of: a constriction amplitude of the pupil as the difference in pupil measurement between a steady state prior to the exposure to the flash of the light source and a minimum measured state of the pupil; a dilation amplitude of the pupil as the difference between a minimum measured state of the pupil and a first turning point during recovery of the pupil; a constriction velocity of a measure of a rate of change of the pupil measurement from the start of the exposure to the flash of the light source to the minimum measured state of the pupil; a dilation velocity of a measure of a rate of change of the pupil measurement from the minimum measured state of the pupil to the first turning point during recovery of the pupil; a general amplitude measure of a pupil from the minimum measured state of the pupil to the maximum measured state of the pupil; and an absolute maximum measured state of the pupil relative to zero.

The method may include measuring a graphical relationship between the constriction amplitude, the constriction velocity, the minimum measured state of the pupil, the dilation velocity, the dilation amplitude, the general amplitude, and the absolute maximum, including fine tuning measurement accuracy.

According to another aspect of the present invention there is provided a system for obtaining a pupil response profile, including a processing system comprising: an input component for obtaining scan data as frames of a pupil response over time prior to, during and after exposure to a flash of a light source; a pupil locating component for locating a candidate pupil to be measured from the scan data; an image processing component for image processing the scan data to obtain a set of pupil candidate measurements to generate a graph of pupil measurements against time; a filtering component for filtering the graph to produce a final set of pupil measurements forming a pupil response profile; a profile parameter component for measuring profile parameters from the pupil response profile; and an output component for using the profile parameters to determine aspects of the pupil response.

The system may include: a scanning apparatus including: a pupil locating light source for applying a light source of a given shape for a defined period to a subject; a visible light source for subsequently applying a flash of a visible light source to the subject; and a pupil scanner for scan data obtains one or more frames with a reflection of the pupil locating light source in an imaged pupil and multiple frames of the imaged pupil prior to, during and after exposure to the flash of a visible light source. The pupil locating light source may be an infra-red light source and may be used for subsequently applying an infra-red background light during the scanning.

The pupil locating component for locating a candidate pupil may include obtaining scan data of a reflection of the pupil locating light source of a given shape from the surface of an eye and locating a pupil identifies a generally circular image including a reflection of the given shape.

The image processing component may include standardising the pupil measurements by using a ratio of a measured pupil size and an estimated pre-calculated ratio of the distance from a camera capturing device to a surface of a subject's eye. Alternatively, the image processing component may include standardising the pupil measurements by using a ratio of a measured pupil size and a measured distance between reflections in the scan data of two eyes of a subject.

The filtering component for filtering the graph filters may use a running averaging filtering to average the pupil measurements to at most a single pupil measurement per time frame removing erroneous pupil measurements, due to brief partial or complete covering of the pupil by the eyelid, to produce a pupil response profile.

The filtering component for filtering the graph may remove noisy measurements through the implementation of a spline line of best fit on the pre-filtered data.

The image processing component for image processing the scan data may include one or more or a combination of: maximally stable external region (MSER), grayscale thresholding, and image column summing and averaging methods to measure pupils.

The profile parameter component for measuring profile parameters from the pupil response profile may include measuring one or more of the group of: a constriction amplitude of the pupil as the difference in pupil measurement between a steady state prior to the exposure to the flash of the light source and a minimum measured state of the pupil; a dilation amplitude of the pupil as the difference between a minimum measured state of the pupil and a first turning point during recovery of the pupil; a constriction velocity of a measure of a rate of change of the pupil measurement from the start of the exposure to the flash of the light source to the minimum measured state of the pupil; a dilation velocity of a measure of a rate of change of the pupil measurement from the minimum measured state of the pupil to the first turning point during recovery of the pupil; a general amplitude measure of a pupil from the minimum measured state of the pupil to the maximum measured state of the pupil; and an absolute maximum measured state of the pupil relative to zero.

The profile parameter component may include a tool for measuring a graphical relationship between the constriction amplitude, the constriction velocity, the minimum measured state of the pupil, the dilation velocity, the general amplitude, the absolute maximum, and the dilation amplitude, including fine tuning measurement accuracy.

The scanning apparatus may include two light emitting diodes as light sources for the flash and an array of infra-red light emitting diodes as a source for both the glint reflection and illumination for the camera in the scanning apparatus enclosure.

The output component for using the profile parameters to determine aspects of the pupil response may be used to detect one of more of the group of: disease, including but not limited to communicable diseases and diabetes; ingestion of a substance; viral or bacterial infection; exposure to a source that affects pupillary muscle function; nerve impairments; and vein, artery or capillary impairments.

According to a further aspect of the present invention there is provided a computer program product for obtaining a pupil response profile, the computer program product configured to: obtain scan data as frames of a pupil response over time prior to, during and after exposure to a flash of a light source; locate a candidate pupil to be measured from the scan data; carry out image processing of the scan data to obtain a set of pupil measurements to generate a graph of pupil measurements against time; filter the graph to produce a final set of pupil measurements forming a pupil response profile; and measure profile parameters from the pupil response profile.

An embodiment of the invention will now be described, by way of example only, with reference to the accompanying drawings.

BRIEF DESCRIPTION OF THE DRAWINGS

In the drawings:

FIGS. 2A and 2B are flow diagrams of example embodiments of aspects of a second stage of a method in accordance with the present invention;

FIG. 3 is a flow diagram of an example embodiment of an aspect of a third stage of a method in accordance with the present invention;

FIGS. 4A and 4B are graphs showing example embodiments of aspects of a fourth stage of a method in accordance with the present invention;

FIG. 5 is a flow diagram of an example embodiment of an aspect of a fourth stage of a method in accordance with the present invention;

DETAILED DESCRIPTION WITH REFERENCE TO THE DRAWINGS

A method and system are described for obtaining a pupil response profile for one, both or an average of the eyes of a subject. The described method and system obtain a pupil response profile with preferably a single pupil measurement point per time frame resulting in an averaged pupil response profile. The pupil response profile may be used to obtain measurements of various parameters which may be used in various applications.

Figure 4A:
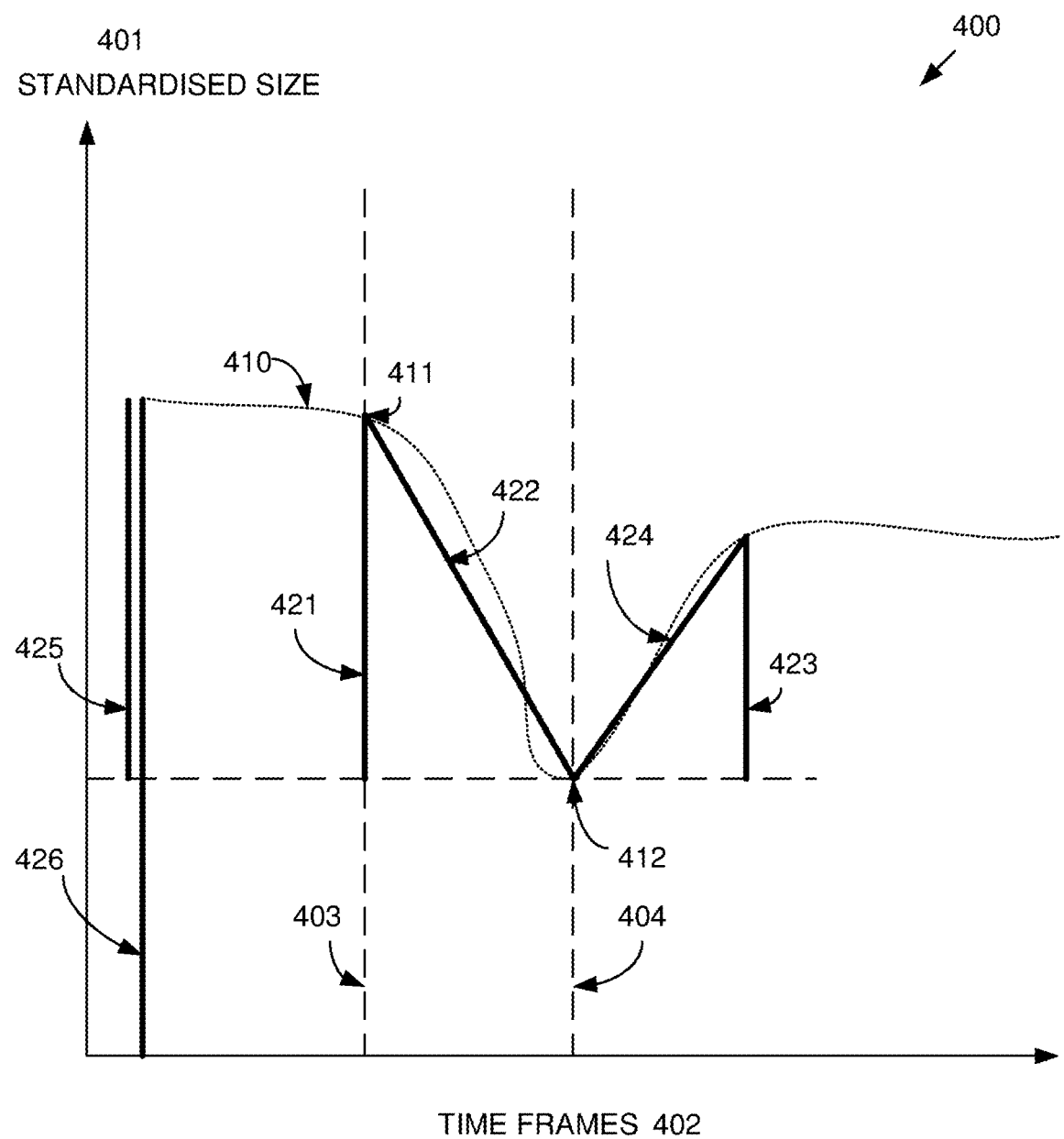

The method may be considered as different stages. In a first stage, illustrated in FIG. 1, a subject may be registered and a scan carried out. In a second stage, illustrated in FIGS. 2A and 2B, the scan data may be processed. In a third stage, illustrated in FIG. 3, the processed data may be stored in relation to the subject. In a fourth stage, illustrated in FIGS. 4A, 4B and 5, comparisons between processed data may be carried out.

Figure 1:
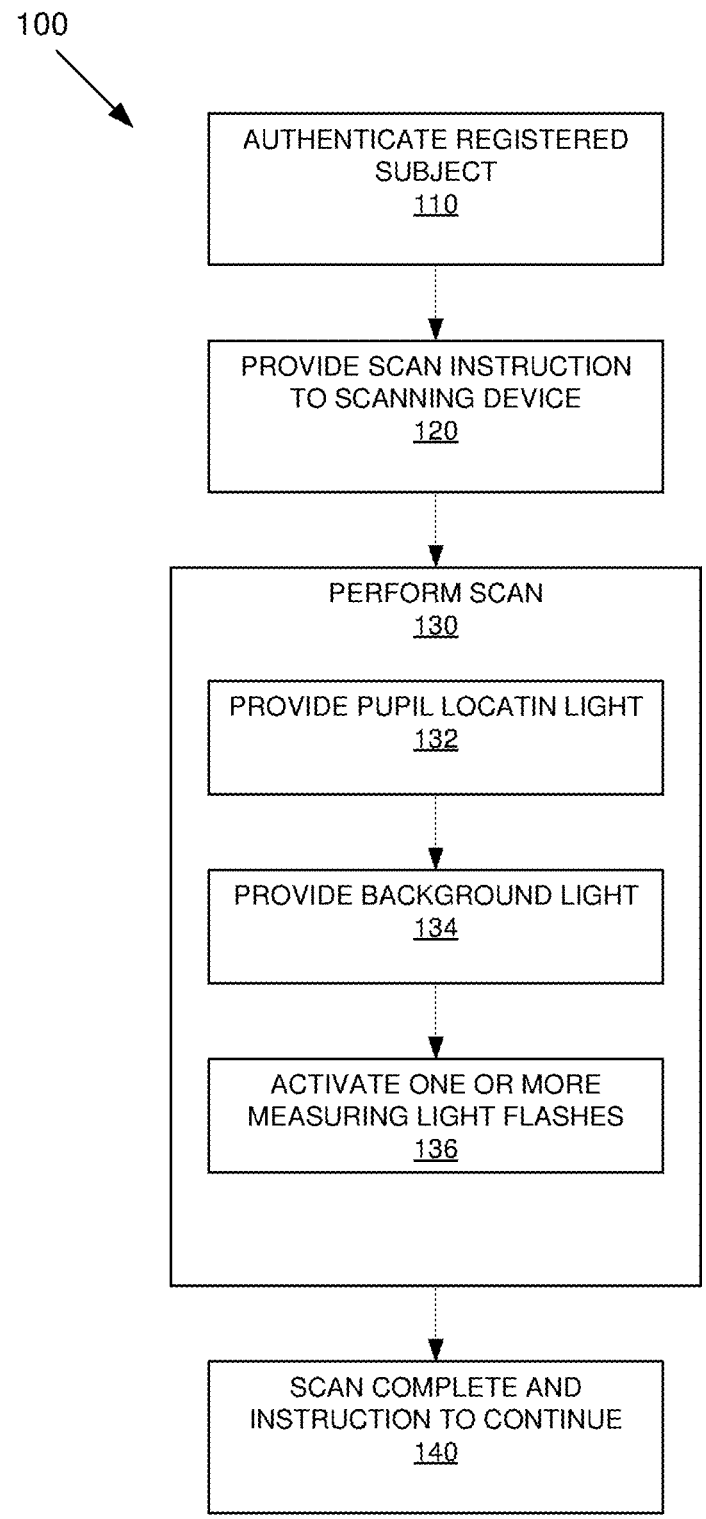
FIG. 1 is a flow diagram of an example embodiment of an aspect of a first stage of a method in accordance with the present invention.

Referring to FIG. 1, a flow diagram (100) shows an example embodiment of an aspect of the described method of registering a subject. Registering a subject may be carried out using an administrative user interface referred to as a dashboard. New subjects are registered on the dashboard, for example, under a subjects' tab. The administrative user interface may be used in conjunction with a scanning device.

A registered subject may have an authentication (110) carried out by a login and may be associated with a fingerprint as input into the scanning device. Once an administrative user has logged onto the scanning device they can take fingerprint scans and register a fingerprint to an existing registered subject on the system. This process associates a fingerprint id (0-199) with a system username, this association may be done on the local scanning device only. This means that the fingerprint will only work on the scanning device with which it was registered.

Scan instruction may be provided (120) to the scanning device, and a scan performed (130) of one or both eyes of the subject. Once the scan is complete, instructions may be provided (140) to continue. The scan performed (130) may involve the subject placing their eyes in relation to the scanning device. The scanning device may be for a single eye and may measure each eye independently or may be for two eyes where each eye is measured independently or simultaneously.

For each eye, the scanning device may have a stimulating light source, a pupil locating light source, a background light source, and a scanning camera. The stimulating light source may be of white light or a selected wavelength or combinations of wavelengths as appropriate to the required stimulation. The pupil locating light source may be an infra-red light source or may use visible wavelengths of light in a selected range; however, the pupil locating light source should not stimulate the pupil response or only stimulate it to a small degree. The background light source may be infra-red light sources and the scanning camera may be an infra-red camera.

The infra-red light source may be emitted by infra-red LEDs that is not visible to the eye. The infra-red light source may have two arrangements for use in two stages of configuration during the scan.

In the first stage, the pupil locating light source is provided (132) for pupil location. This may be an infra-red light source provided in a known shape to obtain a reflection from the surface of the eye which shows in the images captured by the infra-red cameras as a reflection of the known shape in each eye of the subject. In order to locate the eye and thus the pupil, a known shape is created using an array of infra-red LEDs in the required shape. This shape of LEDs is reflected in the eye and allows the software, through the camera, to locate the reflection using templating with the same shape.

The pupil locating light source may be provided as an array of light in a recognisable shape, such as the shape of a square with two planetary dots in order to aid the identification of light reflection against background noise and (usually circular) reflections in skin and eye bumps in a resulting scan.

These reflections are used in the first stage of the scan to locate the centre of each eye of the subject. Once the eyes are located, the pupil locating light source responsible for creating the reflections is disabled and a separate set of infra-red LEDs are enabled to allow the infra-red camera to see the subjects face and eye areas in the dark enclosure.

In a second stage, a background light source is provided (134), such as an infra-red light source for background illumination of the eye area for the scanning camera to see. Infra-red LEDs may be mounted within a scanning enclosure and may be needed throughout the scan illuminating the face and eye areas for the infra-red camera to see. The design of this second stage of infra-red LEDs are such that the least amount of infra-red light is reflected in the pupil area of the subject's eyes.

Interference of the reflection in the pupil of the pupil locating light with the algorithms that get the diameter of the pupil during the scans is required to be minimised. The algorithms rely on a clear image of the hollow of the eye through the pupil opening. Infra-red lighting creates a white reflection on the surface of the eye that may obscure the pupil. The problem is worsened when the pupil is contracted during the test, creating a smaller pupil area which decreases the ratio between white reflection and pupil, increasing the error rate of measurements. The solution is provided of using a two stage infra-red lighting. The first stage shows the infra-red shape required for pupil location, captures one or more frames which are then used to locate the eyes and the pupil. After this initial locating frame or frames, the second stage involves disabling the infra-red locating shape and enabling a second set of LEDs required for the background illumination. The initial location of the pupil may be adjusted through a closed loop feedback system by calculating the difference in location of the pupil centre relative to the current captured frame eye region-of-interest and the centre of the current captured frame eye region-of-interest.

This difference is then passed into the next captured frame pupil calculations, which is used to offset the pupil such that it is centred in said frame.

Disabling the locating infra-red LEDs after a first frame means that the locating infra-red LEDs (which create a large amount of reflected light) do not obstruct the pupil during the sensitive pupil measurement stages of the scan. Moving the background infra-red LEDs from close to the camera to further away means the reflections during the pupil measurement stages of the scan are located on the periphery, or outside, of the iris and not inside the black shape of the pupil.

The stimulating light source may then be activated (136) for supplying a flash of light to stimulate pupillary constriction in the subject. This flash of light may be provided by two visual light emitting diodes (LEDs) either independently or simultaneously, using either single diode LEDs or multi-diode LEDs (such as red-green-blue combinational LEDs) as a stimulus.

The light source providing the stimulus to the eye may provide at least one short flash of light of the order of several milliseconds. The flash of light may be provided to both eyes simultaneously or each eye independently. The stimulating light source may be of a particular range of light wavelengths and two or more light sources may be provided having different ranges of light wavelengths which may be used in subsequent or simultaneous flashes.

The light sources and the scanning device may be a set distance from eyes, for example in the order of 10 to 15 cm, to ensure that the images recorded of the eyes are in focus. The scanning may be carried out by an infra-red camera as this has the advantage of removing data relating to the iris from the scan as well as allowing the pupils of the subject to dilate without medical intervention in a dark environment. The camera may record in the range of 20 to 30 frames per second which is the same order as the reaction time of an eye with the aim to synchronise to the reaction of the eye.

Once a subject has been scanned by the scanning device, the scan data may be saved as a video. This video is associated with details of the scan as well as the subject's details and can contain an overlay of the preliminary results as well as the image processing outputs at the various stages of the processing for the measurement of the pupil. Details of the scan may include the scan settings, such as when and for how long the LEDs were triggered, what colour they were when triggered, the brightness, the frame count, the frame rate, and details about the scan subject and study identifier, amongst other things.

The scan data is processed which involves the assessment and measurement of the subject's pupil sizes using image processing and data filtering algorithms. The processing may be carried out at the scanning device and once the data is processed it may be sent to a backend system (for example, a cloud database) and stored. Due to the reduction in file size due to the processing and filtering of the data, the data may be sent to a remote backend system efficiently and with increased speed. From an online dashboard the data are accessible and from the dashboard it can be measured using metrics outlined below.

Figure 2A:
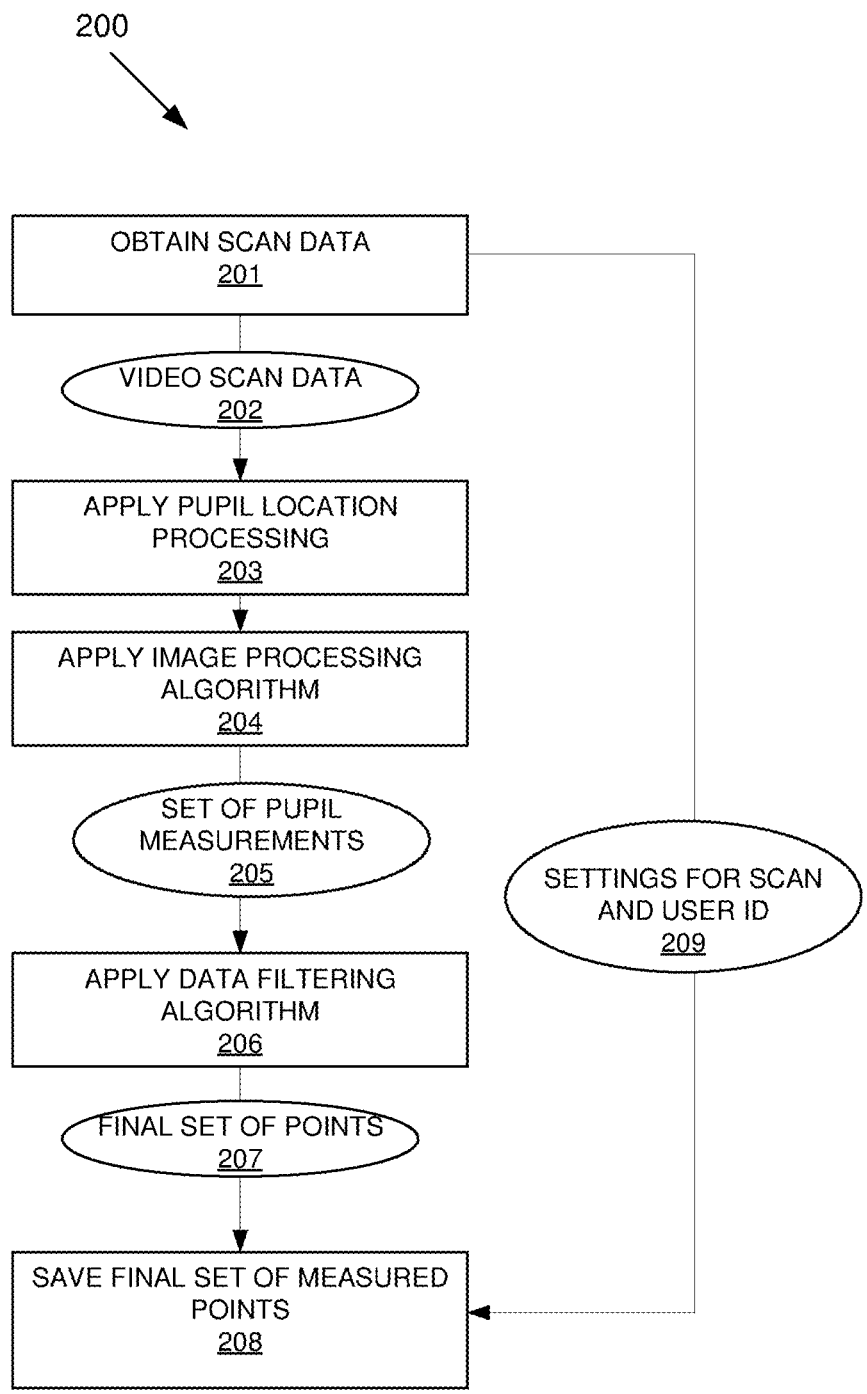

Referring to FIG. 2A, a flow diagram (200) shows an example embodiment of an aspect of the method of the second stage of processing scan data. Unprocessed video scan data (202) may be obtained (201) as frames of a pupil response over time including during the provision of an infra-red locating light source and prior to, during and after exposure to a flash of the stimulating light source. The video scan data (202) may have pupil location processing (203) applied to it and may have an image processing algorithm applied (204) to it to obtain a set (205) of pupil measurements.

The pupil location processing (203) may identify potential eye candidates as potential candidate circles or blobs. Reflections of the known shape created by the use of an array of the infra-red light source in each eye may be identified at the start of the scan and their location stored for further processing. These are used in two ways in the processing. Firstly, potential candidate circles or blobs are removed if they do not have a glint located within them. Candidate circles or blobs which are the pupil will have a reflective glint within their circumference. Secondly, a standardized measurement of pupil candidates may be achieved by using a ratio of the pupil measurement (for example, the diameter or circumference) to the distance measured between reflections from two eyes of a subject as shown on the recorded scan image.

The image processing algorithm may be applied (204) as described further below and a point set of pupil measurements per time frame (205) may be generated. The point set (205) may use a measurement of the ratio of a measured pupil size and the distance between reflections in the scan data of a person's two eyes or a measurement based on the fixed distance from the camera to the interface to the person's eyes. Using this ratio ensures a constant pupil measurement standardised by the distance between the two pupils in the scan data from one scan of the person to the next. Using the standard distance measurement ensures a constant pupil measurement in comparison to a generic baseline set of response features.

A data filtering algorithm may be applied (206) as a point graph filter to the set (205) of measured pupil values to obtain a final set (207) of measured points. The final set (207) of measured points may be saved as a final scan measurement data packet (208) which may also have the settings for the scan and subject ID data (209) saved with it.

Referring to FIG. 2B, a flow diagram (250) shows further details of an example embodiment of an aspect of the method of the second stage of processing scan data. The pupil location processing (203) and image processing algorithm (204), which assesses the video stream frame by frame (251), may be made up of the following steps.

Pupil location processing (203) may be carried out by a thresholding and templating technique used to identify (253) potential glints within hardcoded regions of the captured frames. The hardcoded regions may be defined by the dimensions of the scanning device. When a subject's face is pressed to the scanning device, it is given that the eyes will fall in a certain region of the camera's view. The glints are the reflections of the known shape created by the use of an array of the infra-red light source.

A fall-back of using HAAR Cascade eye detection (252) may be used if the glint is not detected in the hardcoded region above. HAAR Cascade uses digital image features for object recognition.

Once eye candidates have been located, the method may use a combination of methods in an image processing algorithm (204) to create weighted-average pupil measurements. This may be done through machine learning, where the code is be able to apply the weighting dynamically through the measured performance of results from previous frames. The methods may be a combination of one of more of: maximally stable external regions (MSER) methods (255), grayscale thresholding and weighting techniques (256) and vertical averaging techniques (254) of image column summing.

A point graph of pupil candidate measurements per time frame may standardise (257) pupil measurements by either:
- As a ratio of a measured pupil size and a measured distance between glints in the scan data of two eyes of a subject, wherein a glint is caused by a reflection of an infra-red light source on the surface of the eye; or
- As a ratio of a measured pupil size and an estimated pre-calculated ratio of the distance from the camera capturing device to the surface of the eye, provided standard due to the fixed length of the goggle apparatus of the scanning device.

From this processing, a measurement best effort point set, here forth 'point set' may be generated (258). This contains a single measurement for each eye for each time frame, with pre-processing applied from the computer vision portion of the process to increase the probability of creating an accurate measurement.

The data filtering algorithm (206) may be applied (259) to this point set data and the filter removes noisy measurements and filters out a large degree of erroneous data to result in a final set of points (260). The filtering may make use of a standard deviation limit on average deviation to eliminate graph fluctuations and erroneous data caused by the partial or complete covering of the pupil by the subject's eyelid. The filtering may remove noisy measurements through the implementation of a spline line of best fit on the pre-filtered data Further details of the data filtering algorithm is provided below in relation to FIGS. 7A to 7B.

Referring to FIG. 3, a flow diagram (300) shows an example embodiment of the third stage of the method of storing the processed data.

Once a scan has been successfully processed by the scanning device to obtain processed data (301), the data is stored (302) with pre-measurement on a backend server, for example, in a cloud-based server. The data may be sent to the backend server via an HTTP POST request. The data may include:
1. The ID of the subject;
2. A date stamp;
3. The settings with which the device took a scan measurement;
4. The data from the processed video.

Once the scanning device has taken a scan, and processed the results, and the data is uploaded to a backend database. The data may be viewed and measured (303) via a user interface dashboard. Scan data in which a normal set of eyes is exposed to a brief (in the order of a millisecond) flash has a characteristic response curve.

FIG. 4A shows the data (410) plotted as a graph (400) as a pupil size ratio (401) against time (402) in frames. The ratio (401) is the size of the pupil compared to the distance between the array reflections in the eyes. The graph (400) shows a starting time (403) of the light flash and a finishing time (404) of the light flash.

There are six core characteristic measurement parameters which may be taken into consideration.
1. Constriction amplitude (421).
The measure in difference from the light on point (403) or the eye's steady state (411) to the minimum pupil ratio point (412) during the measurement.
2. Constriction velocity (422).
The measure in rate of change, taken from the light on point (403) or the eye's steady state (411) to the minimum pupil ratio point (412) during the measurement.
3. Dilation amplitude (423).
This is the difference between the minimum pupil ratio point (412) during the measurement and the first turning point (413) as the pupil stabilizes.
4. Dilation velocity (424).
This is the rate of change, taken from the minimum pupil ration point (412) to the first turning point (413) on the dilation of the eye.
5. General amplitude (425).
Measurement of the pupil from the minimum measured state of the pupil to the maximum measured state of the pupil.
6. Absolute maximum (426).
Maximum measured state of the pupil relative to zero.

Referring to FIG. 4B, a graph (450), corresponding to the graph of FIG. 4A, shows a five point measurement (460) which can be moved to fine tune measurement accuracy. The five points are a starting point (461), a point at the start of the light on (462), a minimum pupil ratio point (463), a turning point (464) as the pupil stabilizes, and an end point (465). This can be done for both eyes as well as the mean of the eyes.

The data obtained in the form of the pupil response profile and the measured parameters may be used in a wide range of applications. The application may include comparing the two eyes of a subject or comparing to a previous scan of the same subject. The applications may include comparing the profile and parameters with known profiles and parameters for conditions such as diseases, drug and alcohol abuse, etc. Diseases may have different profiles and parameters due to the effect of the disease on the eye's response. The application may include identifying communicable diseases.

In some applications, the scanning device may require that a 'baseline' scan be taken of a subject. The initial scan is taken to be used as a comparative measure. The baseline scan is taken in conjunction with any tests that would prove that the subject is sober or in a 'normal' state. Baseline scans can be taken by administrators, and can be set by control room operators with the correct privileges.

Once a subject is registered and has a baseline, he can be scanned by the device. The new scan will be assessed and the metrics (above) may be compared to the baseline metrics. (i.e. Baseline constriction velocity may be compared to the new scan constriction velocity.)

Scans may consist of a left eye, right eye, and a mean eye value. Automatic assessment takes place on both eyes and the mean. That is to say that the baseline of the left eye is compared to the left eye, etc. The two eyes of a subject may also be compared to each other to obtain details of differences between the eyes. The percentage threshold for the automatic measurement system can be adjusted by the dashboard settings panel.

Control room operators are responsible for cross checking the assessment of the scans. Scan data arrives on the dashboard after it has been stored and automatically assessed. Once the control room operator sees a scan for the first time, it will have been assessed by the automatic measurement system. The system will have marked it as a pass or fail, based on threshold set on the dashboard. Once the system has marked a scan it requires assessment from an operator who additionally to the automatic measurement will assess the scan results. The control room operator may correct for invalid or erroneous measurements taken by the automatic measurement system as sometimes noise on the data will be measured incorrectly.

Input receive from an operator may adjust the pupil response profile and/or parameters. Artificial intelligence and data learning techniques may learn from the user inputs for future automated analysis.

FIG. 5 is a flow diagram (500) showing the measurement and comparison of the processed data.

A processed scan may be received (501) from the scanning device and automatic measurements carried out (502) to obtain measured parameters (503). A baseline scan is accessed (504) for the subject and automatic measurements are (or have previously been) carried out (505) to obtain measured parameters (506) of the baseline scan.

The measured parameters of the current scan and the measured parameters of the baseline scan are compared (507) resulting in an automatic pass/fail (508) depending on configured thresholds of the automated system. In addition, an operator may provide a pass/fail (509).

The described method may compare the pupil response profile with a previously determined pupil response profile of the subject and/or a general pupil response profile of a person with at least partially similar characteristics as the subject.

The method may, in response to determining that a pupil response profile indicates an abnormal pupil response profile, determine a known condition associated with the abnormal pupillary response profile present.

A baseline may enable a measure of deviance from a baseline result set for an individual or group, which serves to indicate impairment of the scan subject. A study may be conducted on a group of individuals to ascertain baseline results which can be correlated with the impairments present in the subjects of the study.

Future scans may be analysed to provide feedback to the system operator as a measure of probability or certainty of a scan subject's impairment through comparison of the current scan subjects results to those of the baselines with deviance rules applied.

The characterised response of the pupillary muscle to light stimulus may be used to detect any of the following:
Non-communicable disease, including but not limited to diabetes;
Communicable disease;
Ingestion of a substance;
Viral or bacterial infection;
Exposure to a source that affects pupillary muscle function;
Nerve impairments; and
Vein, artery or capillary impairments.

Figures 6A, 6B:
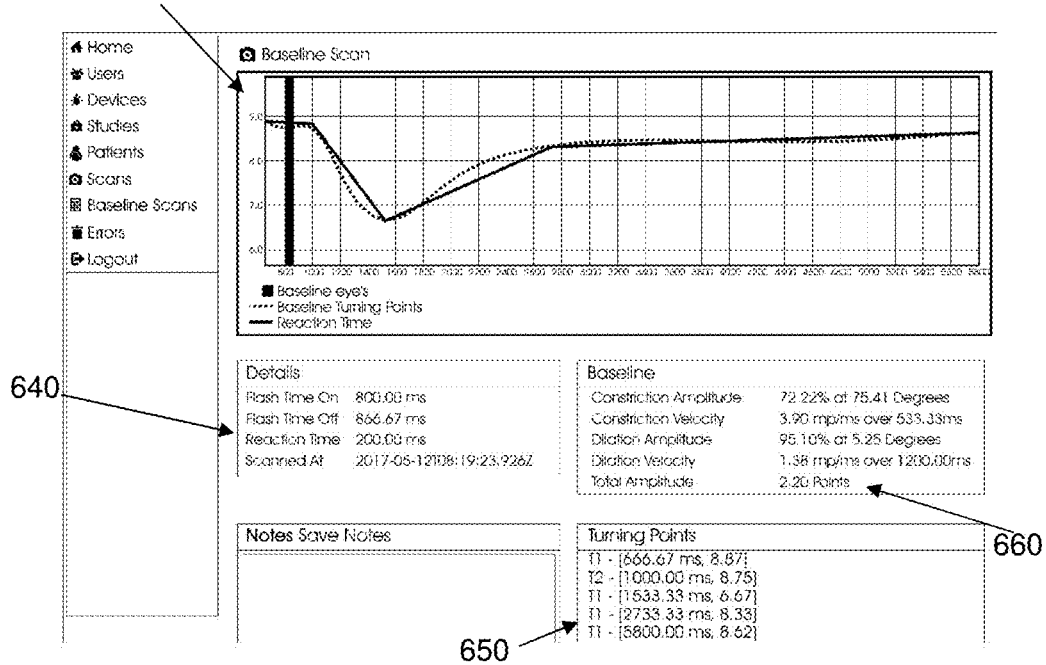
FIGS. 6A and 6B show an example embodiment of a user interface in accordance with an aspect of a fourth stage of a method in accordance with the present invention.

FIG. 6A shows an example user interface (600) showing example measurements and parameters of a scan. Left and right eye divergence thresholds (610) are provided. Baseline divergence thresholds (620) are also provided. The set of thresholds provided in FIG. 6A can be grouped and saved into a rule, which can then be applied to a measurement set, with other rules, to provide analytic feedback to the operator regarding the subject's scanned measurements. The rules can be developed and improved over time with the inclusion of more subject scan data and operator input.

FIG. 6B shows a baseline with the thresholds and parameters visualised in the form of a graph, which is used by the processing system to compare to the parameters of subsequent graphs to provide feedback on divergences. The baseline parameters are shown (640 & 660) for reference. The points of interest on the graph are recorded and shown for reference (650).

Figure 7A:
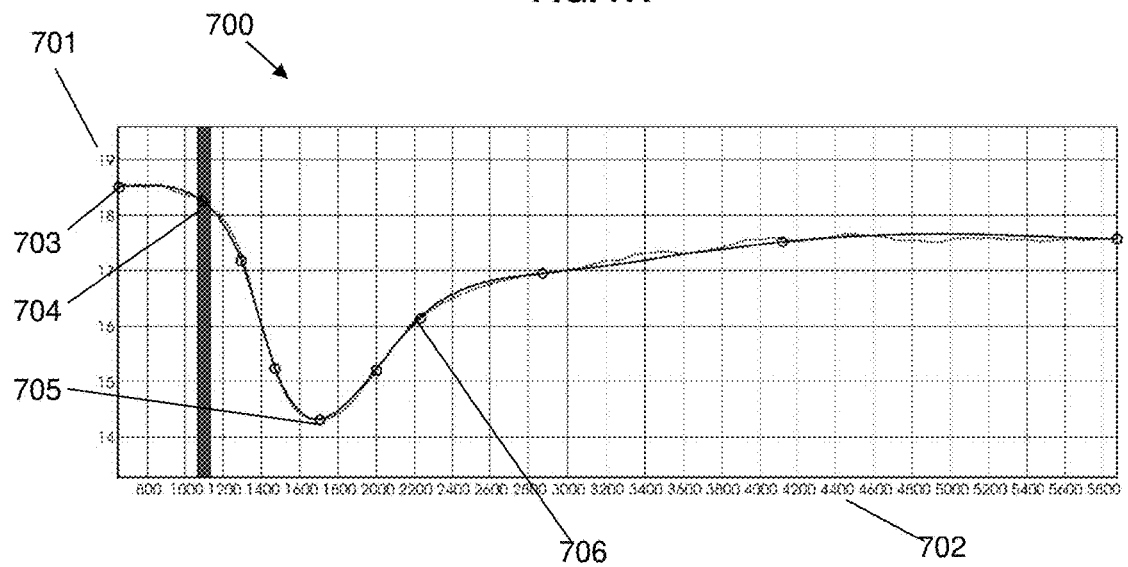
FIGS. 7A and 7B are graphs illustrating an aspect of a processing method in accordance with the present invention.
Figure 7B:
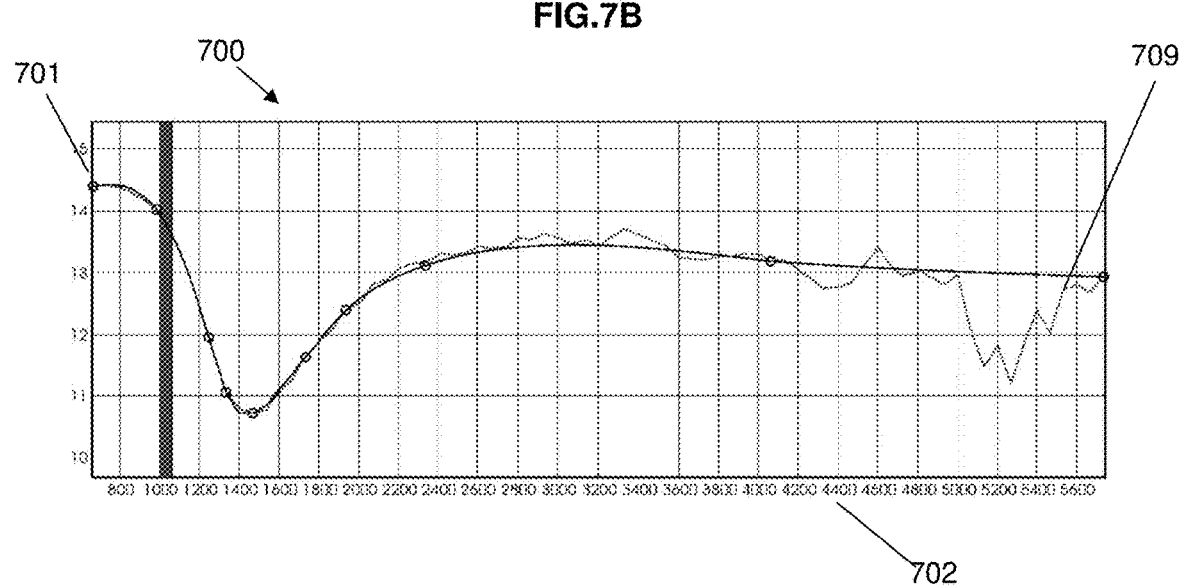

Referring to FIGS. 7A and 7B, further details are now provided of the data filtering algorithm (205) carried out in the data processing stage. FIGS. 7A and 7B show the steps of processing the set of pupil measurements provided in a point set (700) of measured pupil (701) against time frames (702).

From the given point set, strategic points are selected along the length of the unfiltered graph that lie on the points and half-way between points of: the pre-flash steady state (703), the flash midpoint (704), the maximum constriction point (705), the dilation turning point (706) and the post-flash steady state (707).

These points are used in a spline line approximation graph that fits closely to the data set and creates a reliable filter for noisy data points (709), as seen in FIG. 7B.

Traditionally a graph has one measurement value per an axis. The function is something like $F(x)=y$ this implies that for a given value of x there is a singular corresponding value of y, i.e. the straight line graph $y=x$.

This method deviates from this approach in that each value of x has potentially many values of y. This is a more complex method of data visualization.

One method of measuring a value that exists is to simply measure it (find its x) and place it in the context of its y value, where y is a function of x, $(f(x)=y)$. This means that for each point one selected measured value is chosen per another unit of measurement. I.e. if a person were to measure their height in meters as they grow old, there will only ever be one height and a time.

With measurement of the pupil in the described system, there are times when the system will be unsure of the value to use. It has a set of measurement points, but is unsure which point is the correct one.

One approach to improving this would be to improve how the system measures features and points of interest in the image, however there are limitations to this due to the variance of human physiology which is presented, as well as various environmental factors. Some images are not easily identified by a computer, or are hard to single out in the context in which they exist.

The image processing algorithm is pushed to a point where it in general will measure the correct pupil size, however at times it is unsure which measurement is the pupil and which is an erroneous measurement.

These erroneous measurements are partly reduced by a running average on-device filter, which reduces spikes in the measurements.

Figure 8:
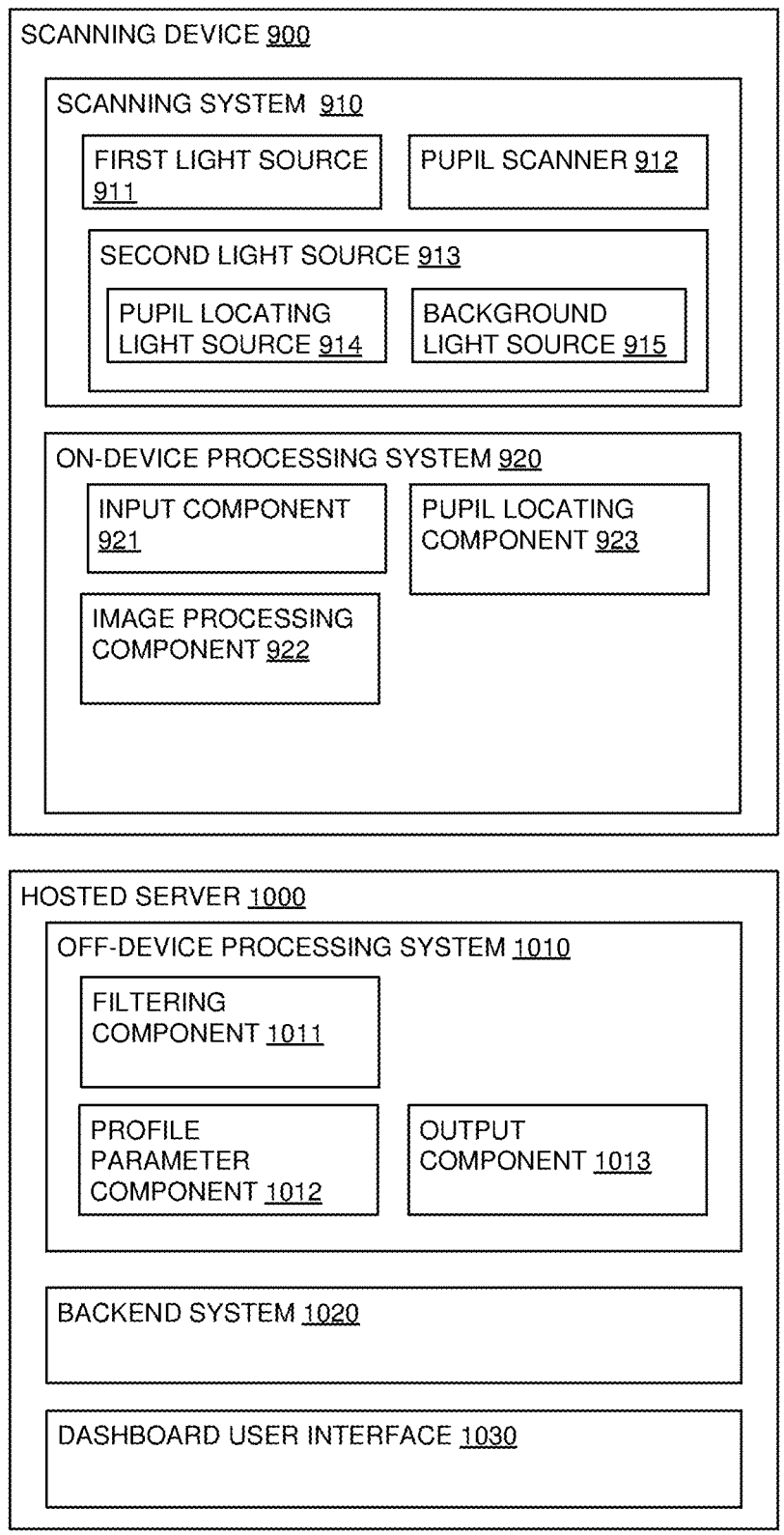
FIG. 8 is a block diagram of an example embodiment of a system in accordance with the present invention.

Referring to FIG. 8, a block diagram shows an example embodiment of the described system (800). The system (800) may include: a scanning device (900) including a scanning system (910) which may include or be in communication with an on-device processing system (920) for processing the data obtained by the scanning device (900); a hosted server (1000) for further off-device processing (1010) and storage of processed data output from the processing system using backend services (1020); and a dashboard user interface (1030) for accessing the processed data of the hosted server (1000) remotely. The processing components may all be provided on-device in an on-device processing system (920), off-device in an off-device processing system (1010), or spread across the two.

The scanning device (900) may include a first light source (911) for providing a stimulating flash of light, and a second light source (913) for providing a pupil locating light source (914) to obtain a reflection from the retina of the eyes and a background source (915) to illuminate the dark interior of the enclosure. The pupil locating light source (914) and the background light source (915) may be infra-red light sources. The infra-red background source may be provided at the extremes of a circuit board and/or on cable connected detached circuit boards located further to the side of an eye goggle enclosure. The scanning device (900) may include a pupil scanner (912) for obtaining scan data as frames of the pupil response over time prior to, during and after the exposure to the flash of the first light source.

The first light source (911) may include one or more light sources of different light wavelength ranges. The pupil scanner (912) may use infra-red light to scan the subject's eyes. The scanning device (900) may include providing a fixed distance between the two eyes during scanning in order to accurately compare measurements over time. The fixed distance is the measure between the two glint points on the eyes and may be provided by the second light source (913) as an array of infra-red light.

The on-device processing system (920) may include an input component (921) for obtaining scan data from the pupil scanner (912) as frames of a pupil response over time prior to, during and after exposure to a flash of the first light source (911).

The on-device processing system (920) may include a pupil locating component (923) for locating a subject's pupil in the scanned image and an image processing component (922) for image processing the scan data to obtain a set of pupil measurements to generate a point graph of pupil measurements per time frame. The pupil locating component (923) may include a Haar cascades classification method and/or a templating and thresholding technique to identifying potential glints in a set of pupil candidates. The image processing component (922) may include components using a combination of the following methods: a maximally stable external region (MSER) method, a column summing and averaging method, and a greyscale thresholding method.

The off-device processing system (1010) may include a filtering component (1011) for filtering the point graph to produce a final set of pupil measurements forming a pupil response profile. The filtering component (1011) may carry out the functionality as described in relation to FIGS. 7A to 7B.

The off-device processing system (1010) may further include a profile parameter component (1012) for measuring profile parameters from the pupil response profile as described in relation to FIGS. 4A and 4B.

The off-device processing system (1010) may also include an output component (1013) for storing the processed data for use via the dashboard user interface to analyse aspects of the pupil response.

In one embodiment, the scanning system (910) and on-device processing system (920) may be provided in a handheld device with wireless connectivity to the hosted backend server (1000) and off-device processing system. It is envisaged that a smart phone having a high resolution camera used as the pupil scanner and a camera flash as the light source may enable a smart phone to provide the functionality of the scanning device (900). Processing may be carried out at the smart phone or the data may be sent remotely for processing.

In another embodiment, the scanning device (900) may be a wall mounted device used for access control via iris recognition or finger print recognition. This wall mounted pupil scanner will perform all outlined pupillary scanning applications and functions. The wall mounted pupil scanner will use the distance between glints of the two eyes as a reference scale to standardize respective pupil sizes in relation to the distance from the scanner.

Figure 9:
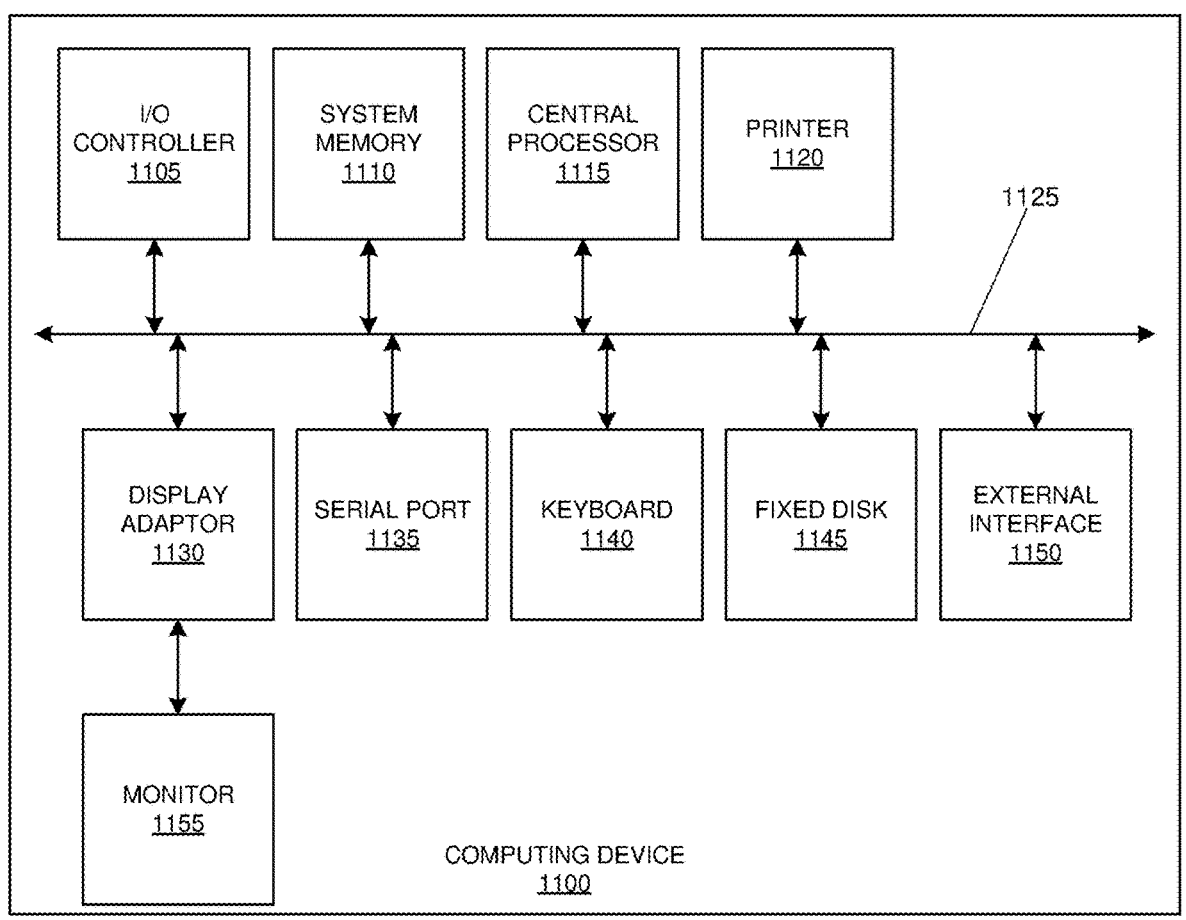
FIG. 9 is a block diagram of a data processing system in which aspects of the present invention may be implemented.

FIG. 9 illustrates an example of a computing device (1100) in which various aspects of the disclosure may be implemented. The computing device (1100) may be suitable for storing and executing computer program code. The various participants and elements in the previously described system diagrams may use any suitable number of subsystems or components of the computing device (1100) to facilitate the functions described herein.

The computing device (1100) may include subsystems or components interconnected via a communication infrastructure (1125) (for example, a communications bus, a cross-over bar device, or a network). The computing device (1100) may include at least one central processor (1115) and at least one memory component in the form of computer-readable media.

The memory components may include system memory (1110), which may include read only memory (ROM) and random access memory (RAM). A basic input/output system (BIOS) may be stored in ROM. System software may be stored in the system memory (1110) including operating system software.

The memory components may also include secondary memory. The secondary memory may include a fixed disk (1145), such as a hard disk drive, and, optionally, one or more removable-storage interfaces for removable-storage components.

The removable-storage interfaces may be in the form of removable-storage drives (for example, magnetic tape drives, optical disk drives, floppy disk drives, etc.) for corresponding removable storage-components (for example, a magnetic tape, an optical disk, a floppy disk, etc.), which may be written to and read by the removable-storage drive.

The removable-storage interfaces may also be in the form of ports or sockets for interfacing with other forms of removable-storage components such as a flash memory drive, external hard drive, or removable memory chip, etc.

The computing device (1100) may include an external communications interface (1150) for operation of the computing device (1100) in a networked environment enabling transfer of data between multiple computing devices (1100). Data transferred via the external communications interface (1150) may be in the form of signals, which may be electronic, electromagnetic, optical, radio, or other types of signal.

The external communications interface (1150) may enable communication of data between the computing device (1100) and other computing devices including servers and external storage facilities. Web services may be accessible by the computing device (1100) via the communications interface (1150).

The external communications interface (1150) may also enable other forms of communication to and from the computing device (1100) including, voice communication, near field communication, Bluetooth, etc.

The computer-readable media in the form of the various memory components may provide storage of computer-executable instructions, data structures, program modules, and other data. A computer program product may be provided by a computer-readable medium having stored computer-readable program code executable by the central processor (1115).

A computer program product may be provided by a non-transient computer-readable medium, or may be provided via a signal or other transient means via the communications interface (1150).

Interconnection via the communication infrastructure (1125) allows a central processor (1115) to communicate with each subsystem or component and to control the execution of instructions from the memory components, as well as the exchange of information between subsystems or components.

Peripherals (such as printers (1120), scanners, cameras, or the like) and input/output (I/O) devices (such as a mouse, touchpad, keyboard (1140), microphone, joystick, or the like) may couple to the computing device (1100) either directly or via an I/O controller (1105). These components may be connected to the computing device (1100) by any number of means known in the art, such as a serial port (1135).

One or more monitors (1155) may be coupled via a display or video adapter (1130) to the computing device (1100).

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. The described operations may be embodied in software, firmware, hardware, or any combinations thereof.

The software components or functions described in this application may be implemented as software code to be executed by one or more processors using any suitable computer language such as, for example, Java, C++, or Perl using, for example, conventional or object-oriented techniques. The software code may be stored as a series of instructions, or commands on a non-transitory computer-readable medium, such as a random access memory (RAM), a read-only memory (ROM), a magnetic medium such as a hard-drive or a floppy disk, or an optical medium such as a CD-ROM. Any such computer-readable medium may also reside on or within a single computational apparatus, and may be present on or within different computational apparatuses within a system or network.

Any of the steps, operations, or processes described herein may be performed or implemented with one or more hardware or software modules, alone or in combination with other devices. In one embodiment, a software module is implemented with a computer program product comprising a non-transient computer-readable medium containing computer program code, which can be executed by a computer processor for performing any or all of the steps, operations, or processes described.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A computer-implemented method for obtaining a pupil response profile of a subject, comprising:
    obtaining scan data as frames of a pupil response over time prior to, during and after exposure to a flash of a light source, wherein one or more of the frames include a reflection of a pupil locating light source of a given shape;
    locating a candidate pupil to be measured from the scan data including identifying a generally circular image including a reflection of the given shape;
    image processing the scan data to obtain a set of pupil measurements to generate a graph of pupil measurements against time, including standardising the pupil measurements by using a ratio of a measured pupil size and a measured distance between respective reflections of the given shape in the scan data of two eyes of a subject;
    filtering the graph to produce a final set of pupil measurements forming a pupil response profile;
    measuring profile parameters from the pupil response profile; and
    using the profile parameters to determine aspects of the pupil response.

2. The method as claimed in claim 1, including:
    applying a pupil locating light source of a given shape for a defined period to a subject; and
    subsequently applying a flash of a visible light source to the subject;
    wherein obtaining scan data obtains one or more frames with a reflection of the pupil locating light source in an imaged pupil and multiple frames of the imaged pupil prior to, during and after exposure to the flash of a visible light source.

3. The method as claimed in claim 1, wherein a HAAR cascade eye detection is used if a reflection is not detected in the scan data.

4. The method as claimed in claim 1, including:
    standardising the pupil measurements by using a ratio of a measured pupil size and an estimated pre-calculated distance from a camera capturing device to a surface of a subject's eye.

5. The method as claimed in claim 1, wherein filtering the graph uses a running averaging filter to average to at most a single pupil measurement per eye per time frame, making use of a standard deviation limit on average deviation to eliminate graph fluctuations and erroneous data caused by the partial or complete covering of the pupil by the subject's eyelid.

6. The method as claimed in claim 1, wherein filtering the graph removes noisy measurements through the implementation of a spline line of best fit on the pre-filtered data.

7. The method as claimed in claim 1, wherein image processing includes one or more or a combination of: maximally stable external region (MSER), grayscale thresholding, and image column summing and averaging methods to measure pupils.

8. The method as claimed in claim 1, wherein measuring profile parameters from the pupil response profile includes measuring one or more of the group of:
    a constriction amplitude of the pupil as the difference in pupil measurement between a steady state prior to the exposure to the flash of the light source and a minimum measured state of the pupil;

a dilation amplitude of the pupil as the difference between a minimum measured state of the pupil and a first turning point during recovery of the pupil;

a constriction velocity of a measure of a rate of change of the pupil measurement from the start of the exposure to the flash of the light source to the minimum measured state of the pupil;

a dilation velocity of a measure of a rate of change of the pupil measurement from the minimum measured state of the pupil to the first turning point during recovery of the pupil;

a general amplitude measure of a pupil from the minimum measured state of the pupil to the maximum measured state of the pupil; and an absolute maximum measured state of the pupil relative to zero.

9. A system for obtaining a pupil response profile, including a processing system comprising:

an input component for obtaining scan data as frames of a pupil response over time prior to, during and after exposure to a flash of a light source, wherein one or more of the frames include with a reflection of a pupil locating light source of a given shape;

a pupil locating component for locating a candidate pupil to be measured from the scan data including obtaining scan data of a reflection of a pupil locating light source of the given shape from the surface of an eye and identifying a generally circular image including a reflection of the given shape;

an image processing component for image processing the scan data to obtain a set of pupil candidate measurements to generate a graph of pupil measurements against time, wherein the image processing component incudes standardising the pupil measurements by using a ratio of a measured pupil size and a measured distance between respective reflections of the given shape in the scan data of two eyes of a subject;

a filtering component for filtering the graph to produce a final set of pupil measurements forming a pupil response profile;

a profile parameter component for measuring profile parameters from the pupil response profile; and an output component for using the profile parameters to determine aspects of the pupil response.

10. The system as claimed in claim 9, including:

a scanning apparatus including:

a pupil locating light source for applying a light source of a given shape for a defined period to a subject;

a visible light source for subsequently applying a flash of a visible light source to the subject; and a pupil scanner for scan data obtains one or more frames with a reflection of the pupil locating light source in an imaged pupil and multiple frames of the imaged pupil prior to, during and after exposure to the flash of a visible light source.

11. The system as claimed in claim 10, wherein the pupil locating light source is an infra-red light source and is used for subsequently applying an infra-red background light during the scanning.

12. The system as claimed in claim 11, wherein the scanning apparatus includes two light emitting diodes as light sources for the flash and an array of infra-red light emitting diodes as a source for both the pupil locating light source to provide a reflection of a given shape and illumination for the camera in the scanning apparatus enclosure.

13. The system as claimed in claim 10, wherein the image processing component incudes standardising the pupil measurements by using a ratio of a measured pupil size and an estimated pre-calculated distance from a camera capturing device to a surface of a subject's eye.

14. The system as claimed in claim 10, wherein the filtering component for filtering the graph uses a running averaging filtering to average the pupil measurements to at most a single pupil measurement per time frame removing erroneous pupil measurements, due to brief partial or complete covering of the pupil by the eyelid, to produce a pupil response profile.

15. The system as claimed in claim 10, wherein the filtering component for filtering the graph removes noisy measurements through the implementation of a spline line of best fit on the pre-filtered data.

16. The system as claimed in claim 10, wherein the profile parameter component for measuring profile parameters from the pupil response profile includes measuring one or more of the group of:

a constriction amplitude of the pupil as the difference in pupil measurement between a steady state prior to the exposure to the flash of the light source and a minimum measured state of the pupil;

a dilation amplitude of the pupil as the difference between a minimum measured state of the pupil and a first turning point during recovery of the pupil;

a constriction velocity of a measure of a rate of change of the pupil measurement from the start of the exposure to the flash of the light source to the minimum measured state of the pupil;

a dilation velocity of a measure of a rate of change of the pupil measurement from the minimum measured state of the pupil to the first turning point during recovery of the pupil;

a general amplitude measure of a pupil from the minimum measured state of the pupil to the maximum measured state of the pupil; and an absolute maximum measured state of the pupil relative to zero.

* * * * *